US007741431B2

(12) United States Patent
Allon et al.

(10) Patent No.: US 7,741,431 B2
(45) Date of Patent: Jun. 22, 2010

(54) LIPOSOMES CONTAINING NOVEL TARGETING AND/OR FUSOGENIC PEPTIDES, PREPARATIONS CONTAINING THEM AND THERAPEUTIC USE THEREOF

(75) Inventors: Nahum Allon, Macabim (IL); Carolyn Chambers, Adelphi, MD (US); Ashima Saxena, Fairfax, VA (US); Bhupendra P. Doctor, Potomac, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 425 days.

(21) Appl. No.: 11/339,404

(22) Filed: Jan. 25, 2006

(65) Prior Publication Data

US 2006/0240091 A1 Oct. 26, 2006

Related U.S. Application Data

(60) Provisional application No. 60/649,034, filed on Feb. 1, 2005.

(51) Int. Cl.
| | |
|---|---|
| *A61K 38/00* | (2006.01) |
| *A61K 38/04* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. ....................... 530/300; 530/325; 530/329; 514/2; 424/1.69

(58) Field of Classification Search ...................... 514/2
See application file for complete search history.

(56) References Cited

U.S. PATENT DOCUMENTS 5,215,909 A 6/1993 Soreq
5,260,276 A * 11/1993 Cody et al. ................... 514/14
5,468,623 A * 11/1995 Ohwaki et al. ............. 435/68.1
5,552,520 A 9/1996 Kim et al.
5,595,903 A 1/1997 Soreq
5,736,509 A 4/1998 Balaji et al.
6,217,886 B1 4/2001 Önyüksel et al.
6,309,633 B1 10/2001 Ekwuribe et al.
6,858,580 B2 2/2005 Ekwuribe et al.
7,153,933 B2 12/2006 Wu et al.
2003/0119719 A1 6/2003 Dinkelborg et al.
2003/0228609 A1 12/2003 Whateley
2004/0067196 A1 4/2004 Brunke et al.
2005/0009847 A1 1/2005 Bertilsson et al.
2005/0244339 A1 11/2005 Jauernig et al.
2006/0240091 A1 10/2006 Allon et al.
2007/0086942 A1 4/2007 Chang et al.

OTHER PUBLICATIONS

Cody et al., "Design of a Potent Combined Pseudopeptide Endothelin-A/Endothelin-B Receptor Antagonist, Ac-dBhg[16]-Leu-Asp-Ile-[NMe]Ile-Trp[21] (PD 156252): Examination of Its Pharmacokinetic and Spectral Properties," J. Med. Chem., 1997, vol. 40, pp. 2228-2240, American Chemical Society, Washington, DC.
Klammt et al., "Cell-free production of G protein-coupled receptors for functional and structural studies," Journal of Structural Biology, vol. 159, 2007, pp. 194-205.
Saito et al., "Percutaneous in vivo gene transfer to the peripheral lungs using plasmid-liposome complexes," Am. J. Phisiol. Lung Cell Mol. Physiol., vol. 279,2000, pp. L651-L657.
Macchia et al., "Toward the rational development of peptidomimetic analogs of the C-terminal endothelin hexapeptide: development of a theoretical model," Il Farmaco, vol. 53, 1998, pp. 545-556, Elsevier.
Rovero et al., "Structure-activity studies on endothelin (16-21), the C-terminal hexapeptide of the endothelins, in the guinea-pig bronchus," Br. J. Pharmacol., 1990, vol. 101, pp. 232-234.

(Continued)

*Primary Examiner*—Maury Audet
(74) *Attorney, Agent, or Firm*—Elizabeth Arwine

(57) ABSTRACT

A novel targeting peptide from the C-terminal of endothelin and/or a novel fusogenic peptide from hemagglutinin are optionally conjugated to the carboxy group of 1,2-dioleoyl-sn-glycero-3-succinate and incorporated into liposomes for therapeutic treatment. The novel targeting peptide directs liposomes to lung cells, and, therefore, is useful for delivering liposomes encapsulating cholinesterase genes, particularly, the human serum butyryl cholinesterase (Hu BChE) gene, as a treatment against nerve agents. It is emphasized that this abstract is provided to comply with the rules requiring an abstract which will allow a searcher or other reader quickly to ascertain the subject matter of the technical disclosure. It is submitted with the understanding that it will not be used to interpret or limit the scope or meaning of the appended issued claims. 37 CFR §1.72(b).

7 Claims, 6 Drawing Sheets

OTHER PUBLICATIONS

Plank et al., "The Influence of Endosome-disruptive Peptides on Gene Transfer Using Synthetic Virus-like Gene Transfer Systems," The Journal of Biological Chemistry, vol. 269, No. 17, Apr. 29, 1994, pp. 12918-12924.

Schreier et al., "Targeting of Liposomes to Cells Expressing CD4 Using Glycosylphosphatidylinositol-anchored gp120," The Journal of Biological Chemistry, vol. 269, No. 12, Mar. 25, 1994, pp. 9090-9098.

Brigham et al., "Expression of Human Growth Hormone Fusion Genes in Cultured Lung Endothelial Cells and in the Lungs of Mice," Am. J. Respir. Cell Mol. Biol., 1993, vol. 8, pp. 209-213.

Puyal et al., "Design of a short membrane-destabilizing peptide covalently bound to liposomes," Biochimica et Biophysica Acta, 1994, vol. 1195, pp. 259-266.

Ashani et al., "Butyrylcholinesterase and acetylcholinesterase prophylaxis against soman poisoning in mice," Biomedical Pharmacology, 1991, vol. 41, No. 1, pp. 37-41.

Broomfield et al., "Protection by Butyrylcholinesterase against Organophosphorus Poisoning in Nonhuman Primates," The Journal of Pharmacology and Experimental Therapeutics, 1991, vol. 259, No. 2, pp. 633-638.

Allon et al., "Prophylaxis against Soman Inhalation Toxicity in Guinea Pigs by Pretreatment Alone with Human Serum Butyrylchlinesterase," Toxicological Sciences, 1998, vol. 43, pp. 121-128.

Jokanović, Role of Carboxylesterase in Soman, Sarin and Tabun Poisoning in Rats, Pharmacology & Toxicology, 1989, vol. 65, pp. 181-184.

Hoekstra et al., "Fluorescence Method for Measuring the Kinetics of Fusion between Biological Membranes," Biochemistry, 1984, vol. 23, pp. 5675-5681.

Dias et al., "Binding characteristics of endothelin $ET_A$ receptors in normal and post-mortem rat lung," Peptides, 2000, vol. 21, pp. 861-869.

Rosenecker et al., "Towards Gene Therapy of Cystic Fibrosis," Eur. J. Med. Res., 1998, vol. 3, pp. 149-156.

* cited by examiner

RBL-2H3 EN-1

RBL-2H3 PLAIN

RBL-2H3 TN-2

A549 EN-1

A549 PLAIN

A549 TN-2

US 7,741,431 B2

LIPOSOMES CONTAINING NOVEL TARGETING AND/OR FUSOGENIC PEPTIDES, PREPARATIONS CONTAINING THEM AND THERAPEUTIC USE THEREOF

BACKGROUND OF THE INVENTION

1. Field of the Invention

The present invention relates generally to cell-specific targeting peptides, to fusogenic peptides, to liposomes containing the cell-specific targeting peptides and/or fusogenic peptides, to methods of making the liposomes, and to therapeutic methods of using the liposomes to treat disorders.

2. Description of Related Art

For the past three decades, targeting drugs, oligonucleotides, and genes to a specific tissue have been one of the fundamental goals of the pharmaceutical industry. Until recently this has been a very elusive problem. One of the fundamental properties of living cells is their ability to sense and respond to their environment. This is accomplished by a specific set of receptors on the cell surface. Identifying the specific binding proteins and defining their specificity is a big stride towards resolving the problem of specific tissue targeting. The binding of targeting peptides to drugs raises many technical problems and in most cases affects the activity of the drug. The encapsulation of drugs in liposomes and other microcapsules give an important boost and opens new lines of research. Encapsulation can deliver a large number of drug molecules that are targeted towards a specific tissue, by protecting them from degradation by enzymes. Accomplishing this goal may reduce or even eliminate side effects by reducing the amount of drug needed and increasing its effectiveness due to its accumulation in the target tissue. Since most of the targeting peptides are water-soluble and the phospholipids are oil soluble, specific linkers and several steps are required for binding these two molecules. The situation gets more complicated when the conjugation of several peptides at different concentrations is required for the delivery of a gene.

Accordingly, it was an object of the present invention to provide a simplified means of incorporating targeting peptides into liposomes.

Another object was to identify new targeting peptides and their target cells.

SUMMARY OF THE INVENTION

These and other objects were met with the present invention, which relates in a first embodiment to an isolated and purified peptide comprising an amino acid sequence selected from the group consisting of:
 (a) SEQ ID NO: 1;
 (b) SEQ ID NO: 2;
 (c) SEQ ID NO: 3; and
 (d) SEQ ID NO: 4.

The present invention relates in a second embodiment to a liposome comprising at least one peptide, which comprises SEQ ID NO: 3.

The present invention relates in a third embodiment to a liposome comprising at least one peptide, which comprises SEQ ID NO: 4.

The present invention relates in a fourth embodiment to a method of preparing a liposome, wherein the method comprises the following steps:
 (a) preparing a solution comprising water, at least one of the abovementioned peptides, and other components of the liposome; and
 (b) manipulating the solution to form the liposome.

The present invention relates in a fifth embodiment to a pharmaceutical composition comprising:
 (a) a plurality of the abovementioned liposomes; and
 (b) a pharmaceutically acceptable carrier.

The present invention relates in a sixth embodiment to a method of treating a disorder in a patient in need thereof, wherein the method comprises administering to the patient at least one of the abovementioned liposomes in an amount effective to treat the disorder, wherein the liposome comprises a payload effective for the treating.

The present invention relates in a seventh embodiment to a method of delivering a therapeutic payload to lung cells, wherein the method comprises the following steps:
 (a) formulating at least one lung cell targeted liposome comprising SEQ ID NO: 1 and at least one therapeutic payload comprising at least one gene encoding a therapeutic protein, at least one antisense oligonucleotide, and/or at least one therapeutic drug; and
 (b) administering the at least one lung cell targeted liposome to a patient in need thereof.

The present invention relates in an eighth embodiment to a method of protecting a patient against the deleterious effects of nerve agent poisoning, wherein the method comprises the following steps:
 (a) formulating at least one lung cell targeted liposome comprising SEQ ID NO: 1 and comprising at least one cholinesterase gene; and
 (b) administering the at least one lung cell targeted liposome to the patient.

BRIEF DESCRIPTION OF THE DRAWINGS

One preferred embodiment or a small number of preferred embodiments of the invention will now be described with reference to the drawings, wherein.

Figure 1:
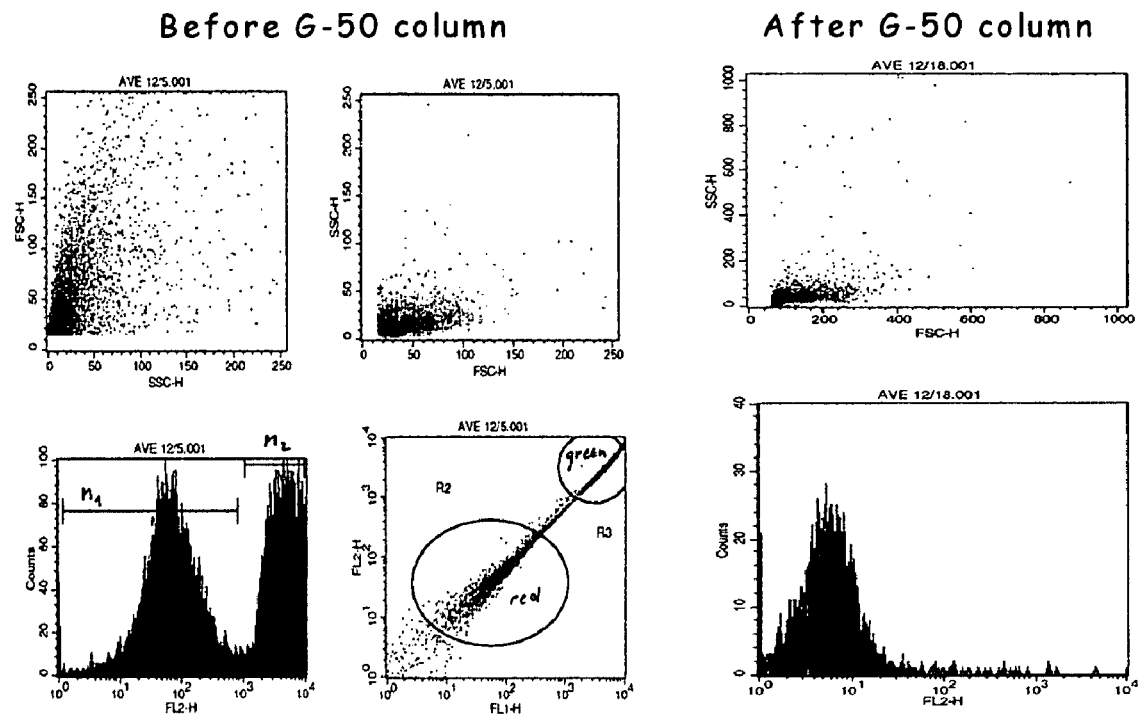
FIG. 1 consists of a series of charts of flow-cytometry measurements of plasmid encapsulated in liposomes before and after purification on G-50 Sephadex column.

It is understood that the references to the drawings herein are meant to be exemplary of the preferred embodiment(s) described, and that neither the drawings themselves, nor the reference numerals on the drawings are meant to be limiting of the invention in any respect.

DETAILED DESCRIPTION OF THE INVENTION

The peptides of SEQ ID NOS: 1-4 can be prepared by well known synthesis schemes, or can be obtained from well known commercial sources. One example of a well known commercial source is SynPep of Dublin, Calif.

By conjugating the N-terminal of either SEQ ID NO: 1 or SEQ ID NO: 2 to the carboxy group of 1,2-dioleoyl-snglycero-3-succinate, new molecules SEQ ID NO: 3 or SEQ ID NO: 4, respectively, are formed.

1,2-dioleoyl-sn-glycero-3-succinate is a well known chemical. It can be prepared by well known synthesis schemes, but is also available from commercial sources. One example of a well known commercial source is Avanti Polar Lipids of Alabaster, Ala.

The amino acid sequence of SEQ ID NO: 1 and SEQ ID NO: 3 derives from endothelin-1 (Dias, L. S. et al. 2000, Rovero, P. et al. 1990), and, surprisingly, it has been discovered that this sequence is an efficient targeting peptide for both lung mast cells and lung epithelial cells. The amino acid sequence of SEQ ID NO: 2 and SEQ ID NO: 4 derives from the amphiphatic, pH-dependent peptide of influenza virus hemagglutinin (Plank, C. et al. 1994), and, surprisingly, it has been discovered that this sequence is highly active as a fusogen. (The terms "fusogen" or "fusogenic," as used herein, mean that the peptide aids the fusion of the liposome with the endosome membrane and the release thereafter of the payload of the liposome into the cytoplasm.) Surprisingly, it has also been discovered that both SEQ ID NO: 3 and SEQ ID NO: 4 are easily incorporated along with other phospholipids into liposomes. Surprisingly, it has further been discovered that the targeting peptide attaches to both the inner and outer surface of the liposomes, and that the presence of the conjugated peptide on the surface of the liposomes improves the efficacy thereof compared to unbound peptide.

Liposome formation technology is well established in the art, and the details thereof will not be repeated here. In general, the inventive liposomes can be prepared by combining at least one of the inventive peptides, preferably one of SEQ ID NO: 3 and/or SEQ ID NO: 4, and other components of the liposome, especially phospholipids, in water to form a solution, and then manipulating the solution to form the liposome. Phospholipids suitable for use in the present invention can be natural phospholipids and/or can be purchased from well known commercial sources, for example, Avanti Polar Lipids of Alabaster, Ala.

In one particularly preferred embodiment, the liposome comprises SEQ ID NO: 3. In another particularly preferred embodiment, the liposome comprises SEQ ID NO: 4. In a very particularly preferred embodiment, the liposome comprises both SEQ ID NO: 3 and SEQ ID NO: 4.

In a preferred embodiment, the liposome encapsulates a therapeutic payload according to well known preparation schemes. In an especially preferred embodiment, the therapeutic payload comprises at least one of:
  (a) a gene encoding a therapeutic protein;
  (b) an antisense oligonucleotide; and
  (c) a therapeutic drug.

Among the different approaches for prophylactic protection against inhaled organophosphorus (OP), the use of exogenous bio-scavengers such as Hu BChE seemed to provide the best protection. The treatment provided protection against multiple lethal doses of nerve agents in mice (Ashani et al. 1991), monkeys (Broomfield et al. 1991), as well as protection against multiple inhaled lethal doses in guinea pigs (Allon et al. 1998). Allon et al. (1998) showed that only 25% of the inhaled OP actually reached the blood, while the remaining 75% of inhaled soman was either exhaled (25%) or retained in the lung. Endogenous scavengers in the lining fluid of the lungs may be sequestering the inhaled soman. Some of the endogenous scavengers are carboxyesterases resident in the lungs and can be manipulated by various drugs such as TOCP (tri ortho cresyl phosphate)or phenobarbitals (Jokanovic 1989) and thus affect the toxicity of various OPs. The lungs may be the first line of defense for the inhaled OPs.

Addition of a bio-scavenger that will be restricted to the lining fluid of the lung may provide an improved protection. According to the present invention, transfecting the epithelial cells with plasmids containing Hu BChE gene may increase the bio-scavenger content of the lungs and thus induce continuous (2-3 week) production and secretion of the enzyme into the lining fluid of the lungs. This may provide the lungs with extended protection against inhaled OPs and reduce the need for repeated injections.

Gene therapy is emerging as a clinically viable therapeutic regimen for genetic, neoplastic and infectious diseases. Originally, gene therapy was aimed at partial or total replacement of a diseased gene, and, thus, at reducing the pathological manifestations of this gene. In recent years a number of models for gene therapy against various pathological manifestations have been presented. These include gene replacement, gene therapy and oligonucleotide therapy (Brigham et al., 1993, Rosenecker et al., 1998). Several approaches for DNA transfection vectors have been used including various viruses' vectors and bacterial plasmid DNA (see review by Schreier, 1994).

The plasmid DNA transfection approach, using liposomes as the gene delivery system, has several advantages, especially when only transient (days or weeks) treatment is required (e.g. destruction of tumor cells or induced protection against inhaled chemical warfare agents). Among the advantages: 1. Convenience of use: Administration via inhaled aerosol. 2. Pharmaceutical universality: A potential for mass production. 3. Safety: Since no viral structure is included and the natural phospholipids are non-immunogenic, a repeated administration can be safe for use as required. 4. Shelf life: Gene encapsulated liposomes can be lyophilized to achieve a prolonged shelf life (Allon et al., 1997). In addition, the bacterial plasmid DNA does not integrate with the host genome, and, thus, is not limited to a specific cell. This transient effect provides better control over the degree and duration of the expression. The Hu BuChE in the lining fluid of the lungs will scavenge the inhaled OP and reduce the amount of OP that enters the blood in similar ratio as endogenous scavengers. In the transfected lungs the cholinesterase activity will be restricted mainly to the lining fluid of the lungs, and, thus, minimize the adverse effects while providing improved protection.

Thus, in one particularly preferred embodiment, the therapeutic payload is a gene encoding a therapeutic protein, especially a cholinesterase. In this embodiment, the gene encoding the therapeutic protein may be contained in a plasmid. In another particularly preferred embodiment, the therapeutic payload is an antisense oligonucleotide. In still another particularly preferred embodiment, the therapeutic payload is a therapeutic drug. In an especially preferred embodiment, the present invention relates to a liposome, which comprises:
  (a) SEQ ID NO: 3;
  (b) SEQ ID NO: 4; and
  (c) a therapeutic payload comprising a gene encoding a cholinesterase. In this especially preferred embodiment, the gene encoding a cholinesterase may preferably encode the human serum butyrylcholinesterase (Hu BChE) gene or the bovine acetylcholinesterase (AChE) gene.

The components to be used to form the inventive liposomes will ordinarily be combined into an aqueous solution, and then this solution will be manipulated according to one of the well known liposome formation techniques to form the liposomes. Preferred liposome formation techniques include sonication, rapid mixing of the liposome components in alcohol, especially ethanol, slow evaporation of an organic solvent from a suspension of the phospholipid in a mixed solvent system, or by reverse dialysis of a detergent from an aqueous solution containing the phospholipid. The reverse dialysis method is especially preferred.

In one especially preferred embodiment, the inventive liposomes are prepared by a method comprising the following steps:
(a) preparing a solution comprising:
 (i) water;
 (ii) one or both of SEQ ID NO: 3 and/or SEQ ID NO: 4;
 (iii) a detergent; and
 (iv) phospholipids; and
(b) subjecting the solution to reverse dialysis to form the liposome.

In another especially preferred embodiment, the inventive liposomes are prepared by a method comprising the following steps:
(a) preparing a solution comprising:
 (i) water;
 (ii) one or both of SEQ ID NO: 3 and/or SEQ ID NO: 4;
 (iii) a detergent;
 (iv) phospholipids; and
 (v) a therapeutic payload comprising a gene encoding a cholinesterase; and
(b) subjecting the solution to reverse dialysis to form the liposome.

Preferably, the solution comprises both SEQ ID NO: 3 and SEQ ID NO: 4

It has been discovered that by conjugating the N-terminal of the newly synthesized targeting or fusion peptide to the carboxyl group of 1,2-dioleoyl-sn-glycero-3-succinate, a new molecule soluble in methanol or methanol-chloroform is formed.

In a preferred embodiment, the amino acid cysteine has been added between the peptide and the liposome surface, and this provides proper spacing and enables the formation of disulfide bonds between two adjacent molecules. This also results in the formation of a double arm active site that improves the efficiency of the targeting and/or fusion process. Liposome formulations containing both fusion peptides and lung cell targeting peptides at concentrations of 0.05-0.5 Mol % are found to be very effective. Utilization of these pre-conjugated phospholipids makes the preparation of the targeting liposomes, at a controlled concentration, easy and reproducible.

The present invention discloses compositions and methods for formulating targeted liposomes for gene, oligonucleotide, or drug delivery. In a preferred embodiment, in those cases where the peptides are heavily charged and the formed molecules are not soluble in methanol:chloroform, liposomes can be formulated and encapsulated by mixing the phospholipids and the peptides in the presence of 8% detergent and using reverse dialysis method to slowly extract the detergent to form liposomes. The method enables the use of two or more conjugated peptides simultaneously without the peptides competing for binding sites.

As noted previously, the present invention can be successfully applied for the delivery of cholinesterase genes, especially, bovine acetylcholinesterase (AChE) and human serum butyryl cholinesterase (Hu BChE) gene, to lung cells for the expression of acetylcholinesterase and butyrylcholinesterase, respectively. This latter enzyme has been tested and evaluated as an antidote for chemical warfare nerve agents.

The cDNA sequences have been cloned for both human AChE and human BChE. See, respectively, U.S. Pat. No. 5,595,903 and U.S. Pat. No. 5,215,909, the entire contents of which are hereby incorporated by reference. These cDNA sequences can be incorporated into suitable vectors, especially bacterial plasmids, for expression in vitro or in vivo. These vectors can be encapsulated within the liposomes of the present invention, and administered to a patient in need thereof to deliver these genes to lung cells where the proteins can be expressed to provide a therapeutic treatment to a patient suffering from the effects of nerve agents.

For therapeutic uses, the inventive liposomes can be administered to a patient in need of treatment according to protocols already well established in the art. In general, a therapeutically effective amount of the liposomes will be combined with a pharmaceutically acceptable carrier. What is a therapeutically effective amount varies depending upon the disorder, the patient and other well known factors such as age, weight, etc., and, thus, must be determined empirically in each case by routine experimentation. In general, the inventive composition can be administered to the patient by any customary administration route, for example, orally, by injection or by inhalation. In the case where the disorder is OP, and the therapeutic payload comprises a gene encoding a chlolinersterase, a preferred dose ranges from about 300 to about 500 μg, but this range can be adjusted as necessary. The pharmaceutically acceptable carrier is any of those already well established in the art. Exemplary pharmaceutically acceptable carriers include, but are not limited to, sterile pyrogen-free water and sterile pyrogen-free saline solution.

In a similar manner, the present invention can also be applied to gene therapy for cystic fibrosis and other genetic disorders of the lung. In this embodiment, preferably, the liposome comprises a therapeutic payload that comprises a gene encoding a therapeutic protein effective against cystic fibrosis or other genetic disorder of the lung, or else the therapeutic payload comprises a therapeutic drug effective against cystic fibrosis or other genetic disorder of the lung.

Further, by selecting the proper targeting peptide, the inventive system can also be applied for targeting drugs or genes in general, to any affected tissue. Since the targeting peptide and the method for pre-conjugation using peptide bonding is simple and reproducible, one can expect it to be useful for any liposome delivery system in the future.

The invention will now be described in greater detail with reference to the following non-limiting examples:

EXAMPLES

Example 1

Material and Methods

Materials:

Phospholipids were purchased from Avanti Polar Lipids (Alabaster, Ala.). Fluorescence dyes for lipids and DNA labeling were purchased from Molecular Probe (Eugene, Oreg.).

Synthesis of Nucleus Localization Peptide (NLP):

The synthesis of NLP is carried out in a protein synthesizer according to specific sequence (Conary et al. 1996). NLP is mixed with the plasmid at ratios between 1:30 to 1:5 (w/w). The ratio that reveals the best expression rate is selected for further research.

Synthesis of Fusogenic Peptides:

Liposomes are picked-up by cells by endocytosis and form an endosome. Within a few minutes the pH in the endosome drops to 5 and degradation begins. In order to accelerate the fusion of the liposome with the endosome membrane and release its DNA content into the cytoplasm, fusogenic peptides (Plank et al., 1994, Puyal et al., 1994), triggered by the low pH, are integrated into the liposomes membrane (0.1-2%). The most suitable fusogenic peptide and its concentration in the liposome are selected, using in-vitro fluorescence method (Hoekstra et al., 1984) at different pH levels.

Liposome Formulations:

Negatively charged liposomes with phospholipids composition similar to membrane of HIV virus are formulated according to (Schreier 1994). Plasmid containing the Hu BChE gene are compressed with synthetic peptide containing nuclear localization signal (Conary et al. 1996) at ratios 1:30 to 1:5 (w/w) and are mixed in the preparation buffer before encapsulation. In order to improve the fusogenisity of the liposome and release the DNA content from the endosome to the endoplasm, a short fusogenic peptide (0.3%-0.5%) bound to phospholipid is added to the formulating mixture. Additionally, a proper targeter peptide is synthesized, tested and incorporated into the formulated liposomes (0.3%-0.5%) via covalent binding to proper phospholipid. Liposomes of 0.2-0.4 µm are prepared by a combination of freeze and thaw (F&T) followed by extrusion (Lipex Bio-membranes Inc., Vancouver) through 0.2-0.4 µm polycarbonate filters. Un-encapsulated payload is removed either via column chromatography (Sephadex G-50) or by centrifugation (30,000 g for 1 h). The encapsulation rate is determined by Flow Cytometry of liposomes with fluorescent payload (DNA fluorescent dye from Molecular Probes).

Results:

Plasmids containing Hu BChE gene, bovine AChE gene or green fluorescent peptide (GFP) gene were encapsulated in small unilamellar vesicles (SUV).

The encapsulation rate was about 60% using NLP (see methods) as compression peptides. Un-encapsulated DNA payload was removed via column chromatography (Sephadex G-50) as demonstrated in FIG. 1.

One of the fundamental properties of living cells is their ability to sense and respond to their environment. This is accomplished by a specific set of receptors on the cell's surface unique to cell type. Specific molecules in the extracellular fluid bind to these receptors and in most cases are taken rapidly into the cells. The process is called receptor-mediated endocytosis.

Figure 2:
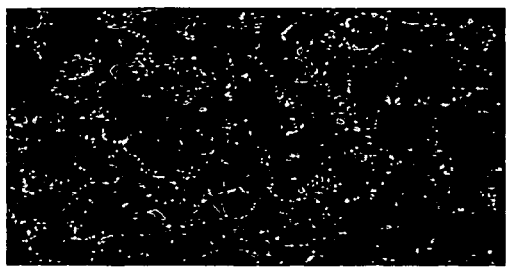
FIG. 2 consists of a series of images demonstrating the efficiency of the targeting peptides in binding to two of the most abundant cell types in the lungs—lung epithelial cells and mast cells.
Figure 2:
Figure 2:
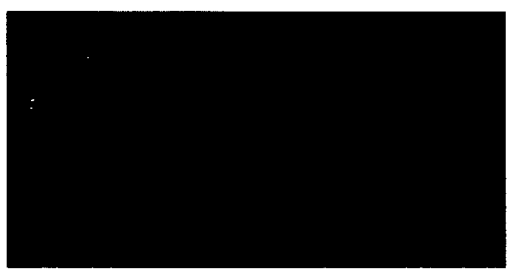
Figure 2:
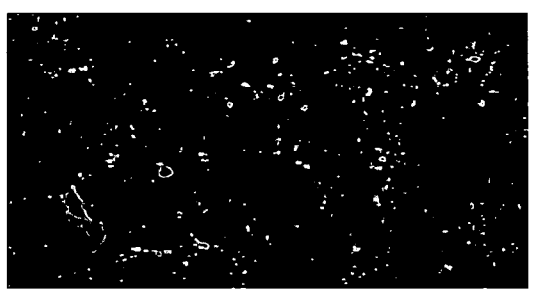
Figure 2:
Figure 2:

Addition of targeting peptide to the liposome delivery system is crucial for overcoming the intrinsic biological barriers awaiting any delivery system to the lungs (e.g. nasal filtration, mucociliary clearance and macrophages). The targeting was meant to bind the liposomes to a specific tissue with high affinity and thus accelerate binding and enhance intracellular uptake. FIG. 2 demonstrates the efficiency of the targeting peptides in binding to two of the most abundant cell types in the lungs: lung epithelial cells and mast cells.

Figure 3:
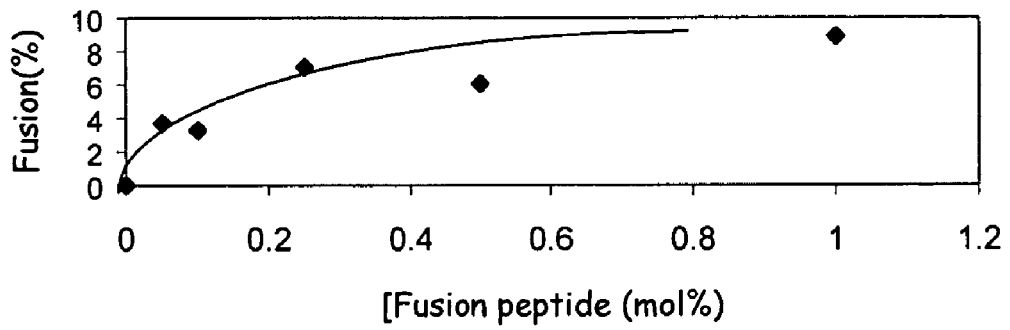
FIG. 3 consists of two graphs demonstrating the fusion of liposomes conjugated with fusion peptide and targeting peptide.
Figure 3:
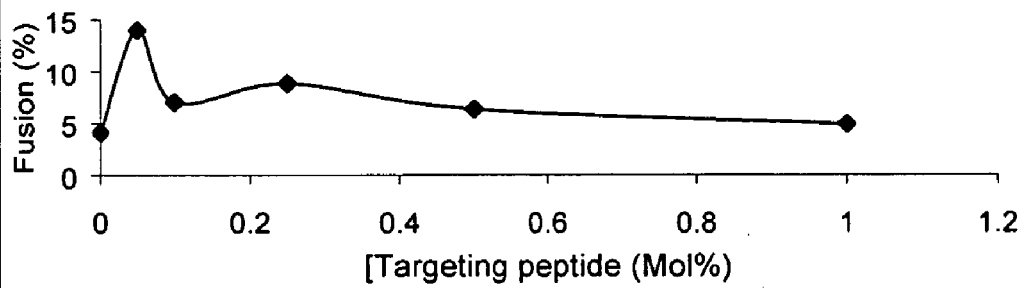

Endosomal Escape:

Following receptor mediating endocytosis, an endosome is formed and within 15 minutes its internal pH drops to pH=5.0. This process is followed by infiltration of degradation enzymes forming a lysosome. In order to release the DNA from the endosome, a fusion peptide, a 23 amino acid length portion of hemagglutinin was synthesized, conjugated to phospholipid via covalent bonding and incorporated into the liposomes at various concentrations. The conjugated liposomes were found quite efficient in fusion to naked liposomes at pH=5.0 with practically no fusion at pH=7.4. Conjugating targeting peptide to the same liposome did not interfere with the fusogenic capacity of the liposomes at low pH as can be seen in FIG. 3.

Figure 4:
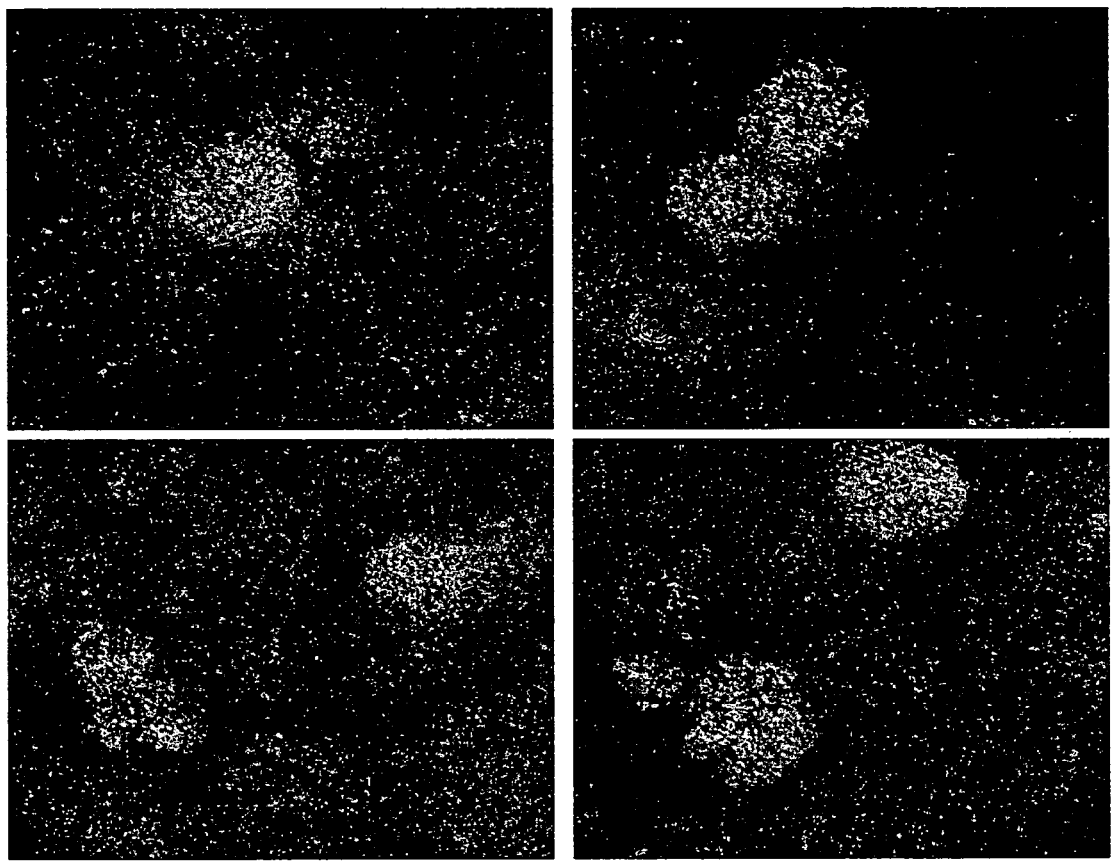
FIG. 4 is a confocal microscope representation of the distribution of DNA (green) and liposome membrane (red) post transfection of RBL cell line.

A double labeling method is used to follow the fate of the plasmid DNA and the phospholipids membrane. Plasmid is labeled with TOTO-1 and the membrane is labeled with Texas Red (TR). The encapsulated liposomes are incubated with cell lines at 40-80% confluency for 30 minutes followed by intensive washes. The labeled DNA (light green) is evenly distributed in the cell's cytoplasm while the phospholipids (red) are concentrated close to the cell's membrane (see FIG. 4).

Figure 5:
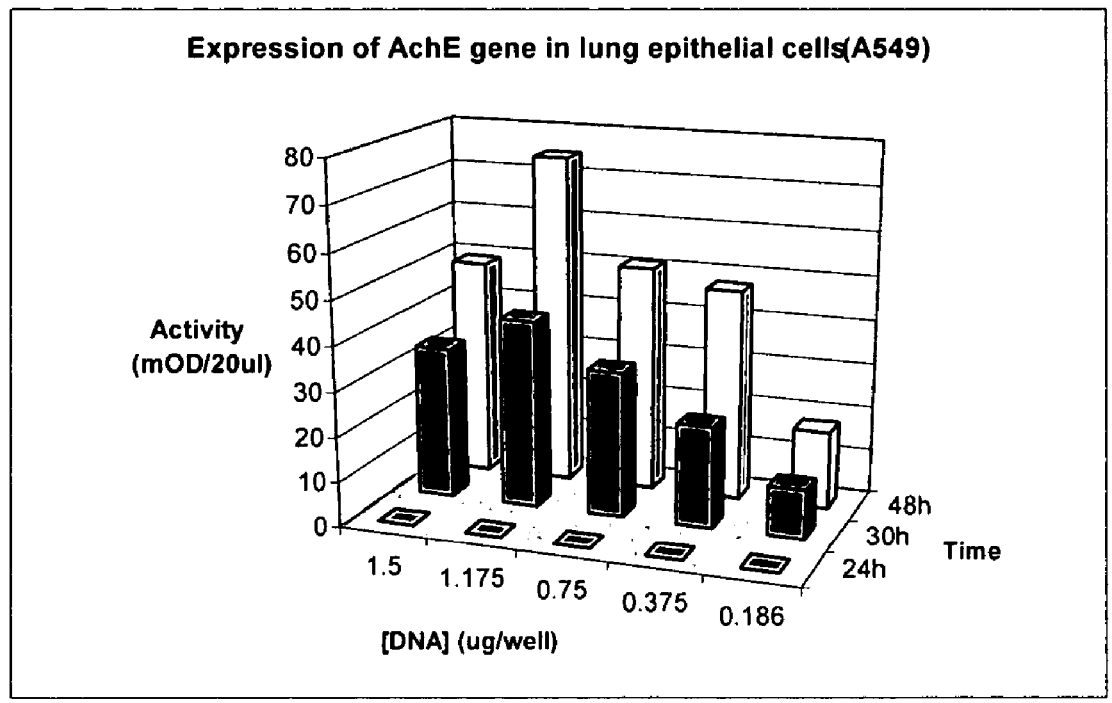
FIG. 5 is a graph depicting secretion of AChE enzyme in A549 human lung epithelial cells.

Transient Transfection Expression:

Three plasmids containing Hu BChE gene, bovine AChE gene or green fluorescent peptide (GFP) gene were cloned and tested for expression in A549 lung epithelial cell line using LipofectAmine 2000 as transfection reagent. In order to measure the expression at different time intervals, the cholinesterase enzymes secreted by the cells into the media were analyzed. Samples of 20 µl were mixed with 1 mM DTNB (5,5'-dithiobis-2-nitrobenzoic acid) and 0.5 mM acetylthiocholine iodine in phosphate buffer, pH=8.0. Notable expression of AChE but not Hu BChE gene was observed in A549 cell line (FIG. 5).

Figure 6:
FIG. 6 is confocal microscope representation of the expression of GFP gene in lung epithelial cells post transfection.

Hu BChE was expressed and secreted in CHO-K1 cell line but not in lung epithelial cells. The GFP gene was also expressed in A-549 cell line (FIG. 6).

Example 2

Materials and Methods

Materials:

Cholesterol (Ch), 1,2-dioleyl-sn-glycero-3-phosphocholine (DOPC), 1,2-dioleyl-sn-glycero-3-phosphoethanolamine (DOPE), sphingomyelin (SM), phosphatidylserine (PS), phosphatidylinositol (PI) and 1,2-dioleoyl-sn-glycero-3-succinate (DGS) are purchased from Avanti Polar Lipids (Alabaster, Ala.). Alpha lactose monohydrate is from Sigma (St. Louis, Mo.). The fluorescence markers used in this study are Texas Red, Rhodamine B (R18) and Toto-1 from Molecular Probes (Eugene, Oreg.). Specific peptides are synthesized by SynPep (Dublin, Calif.).

Liposome Formulations:

Liposomes are prepared as follows: Basic composition of artificial virus envelope (AVE) Ch/DOPC/DOPE/SM/PS/PI molar ratio of 5/1.3/1.26/1.4/0.87/0.13 is prepared in 50 mM phosphate buffer saline (PBS), pH 7.25±0.07. The conjugated targeting peptide as well as the fusion peptide are added to the mixture at various ratios. Fluorescence markers for the lipid layer (0.05-0.1% Texas Red) and for fusion test (R18) are incorporated into the lipid layer during the formation of the initial lipid mixture. Fusion peptides are tested using either mixed with the payload, or incorporated into the lipid layer conjugated to either DOPE (using SPDP [N-succinimidyl-3-(2-pyridyldithio)propionate] for conjugation) or pre-conjugated to DGS.

The plasmid containing Hu BChE cDNA complexed with the synthetic peptide containing the nuclear localization signal above (SynPep) at ratios of 30:1 to 5:1 (w/w) unlabeled or labeled with 0.1% of Toto-1, is mixed in the preparation buffer before encapsulation into the liposomes. The lipid: DNA ratio is 200:1.

Liposome Preparation:

The lipid mixture is dried in a round-bottom flask on a rotatory evaporator followed by hydration in PBS solution (sterilized through a 0.2 µm filter) to a final concentration of 20 mg phospholipid/ml, on a shaker. Each preparation undergoes 5 cycles of freeze and thaw (F&T) followed by extrusion through 800 nm polycarbonate filters. This is followed by 5 cycles of F&T and extrusion through 400 nm and 200 nm (twice) polycarbonate filters respectively. The size of the liposomes after the last step is around 175 nm. Un-encapsulated payload is removed via column chromatography on a Sephadex G-75 column equilibrated in encapsulating buffer saturated with nitrogen prior to the beginning of chromatography. The volume of liposomes eluting in the void volume is adjusted to its original volume using forced dialysis against the original nitrogen saturated solution using a hollow fiber concentration system (Spectrum, Houston, Tex.) or by centrifugation using Centricon concentrators (Amicon, Danvers, Mass.).

Flow Cytometry:

The encapsulation rate for liposomes of various sizes is measured using a flow cytometry scanner.

Conjugation of the Fusion Peptide and Targeting Peptide to Liposomes:

The peptides are synthesized by SynPep according to our specific request and formulation. All peptides are synthesized with Cys at the N-terminal. Conjugations of peptides to 1,2-dioleoyl-sn-glycero-3-succinate are performed immediately after synthesis. The effectiveness of the conjugated fusion peptide is compared to either soluble peptide or peptide conjugated to liposomes formulated with phosphatidylethanolamine previously conjugated to S—S pyridine followed by 17 h incubation of the peptide with Cys at the N-terminal, using the conventional method (Martin, et al. 1994).

Liposome Fusion Assay:

Rhodamine B (R18) quenching curve: Rhodamine is characterized by self-quenching, which increases linearly with increasing concentration of R18. As seen in the quenching curve, a concentration of 9 Mol % resulted in 100% quenching. Fusion tests are performed between liposomes containing R18 at a concentration that would result in about 95% quenching and liposomes that did not contain R18. A total fusion of the two types of liposomes would result in a reduction of R18 concentration or quenching by ~50%. Since liposomes also tend to fuse with their own type, this high level of fusion can never be achieved. The fusion peptides are bound to liposomes that did not contain R18 and the total fluorescence is measured after treating liposomes Triton X-100 (0.1%).

Test Procedure:

Liposomes containing 8 Mol % of R18 are mixed with liposomes conjugated to the fusion peptide at pH 7.4 and the fluorescence is measured using absorbance at $\lambda=550$ nm and emission at $\lambda=580$ nm. The pH is adjusted to 5.0 by adding few drops of 1N HCl and the change in fluorescence is measured. The total fluorescence is then determined by treating the mixture with Triton X-100. Fusion peptides are either free in the media or conjugated to the non-fluorescent liposomes. Due to the high levels of R18 only concentrations of 50 nmol lipid/ml could be tested.

Discussion:

A gene delivery system to lung cells, based on targeted liposomes is designed and formulated. The plasmid is encapsulated in liposomes that are formulated using phospholipids that are pre-conjugated with targeting and fusion peptides. Of the six putative targeting peptides, EN-1 (SEQ ID NO: 2) is selected. The targeting peptide conjugated to the liposomes binds with high affinity to both mast cells (RBL-2H3) and lung epithelial cells (A-549). The 23 aa portion of hemagglutinin was selected as the fusion peptide, and coupled to cysteine. The conjugation of this peptide to phospholipid through a spacer before formulation improved its fusogenic efficiency and reduced the concentration of peptide required for fusion. It should be noted that reproducible liposomes with fusion and targeting peptides could so far be obtained only when both peptides are pre-conjugated to phospholipids. Post-conjugation using SPDP [N-succinimidyl-3-(2-pyridyldithio) propionate] or SMPB [succinimidyl-4-(p-maleimidophenyl) butyrate] as a linker (Martin et al., 1990) gives unreliable and un-reproducible results especially when two different peptides compete for the same binding site. The rate of encapsulation of the plasmid is about 60%. Non-encapsulated plasmid is removed using colunm chromatography. In order to improve the rate of encapsulation and transcription, plasmids are compressed using poly-lysine with nuclear targeting signal (Conery et al. 1996).

Three plasmids containing Hu BChE gene, bovine AChE gene or green fluorescent peptide (GFP) gene are cloned and tested for expression in A549 lung epithelial cell line. Notable expression of both AChE and GFP genes but not Hu BChE gene is observed. For bovine AChE, the enzyme is not merely synthesized but also secreted into the medium within 24 hours.

It should be understood that the preceding is merely a detailed description of one preferred embodiment or a small number of preferred embodiments of the present invention and that numerous changes to the disclosed embodiment(s) can be made in accordance with the disclosure herein without departing from the spirit or scope of the invention. The preceding description, therefore, is not meant to limit the scope of the invention in any respect. Rather, the scope of the invention is to be determined only by the appended issued claims and their equivalents.

What is claimed is:

1. An isolated and purified peptide comprising the amino acid sequence selected from the group consisting of:
   (a) Cys-Gly-Tyr-Trp-Gly-Asp-Ile-Met-Gly-Glu-Trp-Gly-Asp-Glu-Ile-Phe-Gly-Glu-Ile-Ala-Gly-Phe-Leu-Gly (SEQ ID NO: 2);
   (b) 1,2-dioleoyl-sn-glycero-3-succinate-Cys-His-Leu-Asp-Ile-Ile-Trp (SEQ ID NO: 3); and
   (c) 1,2-dioleoyl-sn-glycero-3-succinate-Cys-Gly-Tyr-Trp-Gly-Asp-Ile-Met-Gly-Glu-Trp-Gly-Asp-Glu-Ile-Phe-Gly-Glu-Ile-Ala-Gly-Phe-Leu-Gly (SEQ ID NO:3).

2. The isolated and purified peptide according to claim 1, which is 1,2-dioleoyl-sn-glycero-3-succinate-Cys-His-Leu-Asp-Ile-Ile-Trp (SEQ ID NO: 3).

3. The isolated and purified peptide according to claim 1, which is 1,2-dioleoyl-sn-glycero-3-succinate-Cys-Gly-Tyr-Trp-Gly-Asp-Ile-Met-Gly-Glu-Trp-Gly-Asp-Glu-Ile-Phe-Gly-Glu-Ile-Ala-Gly-Phe-Leu-Gly (SEQ ID NO:4).

4. A liposome comprising at least one peptide according to claim 1.

5. The liposome according to claim 4, which comprises 1,2-dioleoyl-sn-glycero-3-succinate-Cys-His-Leu-Asp-Ile-Ile-Trp (SEQ ID NO:3).

6. The liposome according to claim 4, which comprises 1,2-dioleoyl-sn-glycero-3-succinate-Cys-Gly-Tyr-Trp-Gly-Asp-Ile-Met-Gly-Glu-Trp-Gly-Asp-Glu-Ile-Phe-Gly-Glu-Ile-Ala-Gly-Phe-Leu-Gly (SEQ ID NO: 4).

7. The liposome according to claim 4, which comprises both 1,2-dioleoyl-sn-glycero-3-succinate-Cys-His-Leu-Asp-Ile-Ile-Trp (SEQ ID NO: 3) and 1,2-dioleoyl-sn-glycero-3-succinate-Cys-Gly-Tyr-Trp-Gly-Asp-Ile-Met-Gly-Glu-Trp-Gly-Asp-Glu-Ile-Phe-Gly-Glu-Ile-Ala-Gly-Phe-Leu-Gly (SEQ ID NO:4).

* * * * *

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Cys His Leu Asp Ile Ile Trp
1               5

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Gly Tyr Trp Gly Asp Ile Met Gly Glu Trp Gly Asp Glu Ile Phe
1               5                   10                  15

Gly Glu Ile Ala Gly Phe Leu Gly
            20

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1,2-dioleoyl-sn-glycero-3-succinate conjugated
      to cysteine

<400> SEQUENCE: 3

Cys His Leu Asp Ile Ile Trp
1               5

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1,2-dioleoyl-sn-glycero-3-succinate conjugated
      to cysteine

<400> SEQUENCE: 4

Cys Gly Tyr Trp Gly Asp Ile Met Gly Glu Trp Gly Asp Glu Ile Phe
1               5                   10                  15

Gly Glu Ile Ala Gly Phe Leu Gly
            20
```